(12) United States Patent
Nishiumi et al.

(10) Patent No.: US 12,104,041 B2
(45) Date of Patent: Oct. 1, 2024

(54) BIODEGRADABLE RESIN PARTICLES AND EXTERNAL PREPARATION INCLUDING THE SAME

(71) Applicant: SEKISUI KASEI CO., LTD., Osaka (JP)

(72) Inventors: Kengo Nishiumi, Osaka (JP); Shinya Matsuno, Osaka (JP)

(73) Assignee: SEKISUI KASEI CO., LTD., Osaka (JP)

( * ) Notice: Subject to any disclaimer, the term of this patent is extended or adjusted under 35 U.S.C. 154(b) by 510 days.

(21) Appl. No.: 17/622,392

(22) PCT Filed: Jun. 25, 2020

(86) PCT No.: PCT/JP2020/024938
§ 371 (c)(1),
(2) Date: Dec. 23, 2021

(87) PCT Pub. No.: WO2020/262509
PCT Pub. Date: Dec. 30, 2020

(65) Prior Publication Data
US 2022/0356326 A1   Nov. 10, 2022

(30) Foreign Application Priority Data
Jun. 28, 2019   (JP) .................... 2019-121383

(51) Int. Cl.
*C08J 9/28* (2006.01)
*A61K 8/19* (2006.01)
(Continued)

(52) U.S. Cl.
CPC .......... *C08K 5/06* (2013.01); *A61K 8/19* (2013.01); *A61K 8/85* (2013.01); *A61Q 1/12* (2013.01);
(Continued)

(58) Field of Classification Search
None
See application file for complete search history.

(56) References Cited

U.S. PATENT DOCUMENTS

2012/0312490 A1* 12/2012 Blum ............... D21H 17/63
428/407
2015/0231055 A1   8/2015 Ito et al.
(Continued)

FOREIGN PATENT DOCUMENTS

CN   105008434   10/2015
EP   3 305 833   4/2018
(Continued)

OTHER PUBLICATIONS

Chinese Office Action issued Sep. 20, 2022 in corresponding Chinese Patent Application No. 202080026893.0, with English translation.
(Continued)

*Primary Examiner* — Dominic Lazaro
(74) *Attorney, Agent, or Firm* — Wenderoth, Lind & Ponack, L.L.P.

(57) ABSTRACT

Biodegradable resin particles including a polyhydroxy alkanoate. In the biodegradable resin particles, an amount of a Ca component present in the particles is 10 to 10,000 ppm, the biodegradable resin particles have a volume average particle diameter of 2 to 50 μm, the biodegradable resin particles have a BET specific surface area of 0.8 to 10 m²/g, and the biodegradable resin particles have a linseed oil absorption of 50 to 300 ml/100 g. The resin particles of the present invention can be suitably used by being included in an external preparation, such as a cosmetic or a quasi-drug.

8 Claims, 1 Drawing Sheet

(51) Int. Cl.
    *A61K 8/85*     (2006.01)
    *A61Q 1/12*     (2006.01)
    *A61Q 17/04*     (2006.01)
    *A61Q 19/10*     (2006.01)
    *C08J 3/14*     (2006.01)
    *C08K 3/26*     (2006.01)
    *C08K 5/06*     (2006.01)

(52) U.S. Cl.
    CPC ............ *A61Q 17/04* (2013.01); *A61Q 19/10* (2013.01); *C08K 3/26* (2013.01); *A61K 2800/412* (2013.01)

(56) References Cited

U.S. PATENT DOCUMENTS

2017/0042786 A1     2/2017   Griffiths-Brophy et al.
2018/0265663 A1*   9/2018   Kuwagaki ................ A61Q 1/02

FOREIGN PATENT DOCUMENTS

| | | |
|---|---|---|
| JP | 2016-102152 | 6/2016 |
| JP | 2016-222897 | 12/2016 |
| JP | 2017-2291 | 1/2017 |
| JP | 2018-95794 | 6/2018 |
| JP | 2018/522059 | 8/2018 |
| WO | 2009/129499 | 10/2009 |
| WO | 2017/056908 | 4/2017 |
| WO | 2017/195108 | 11/2017 |
| WO | 2018/178899 | 10/2018 |

OTHER PUBLICATIONS

Extended European search report issued Jun. 21, 2023 in European Patent Application No. 20833604.0.

B. Duan, et al., "Synthesis of Ca—P nanoparticles and fabrication of Ca-P/PHBV nanocomposite microspheres for bone tissue engineering applications," Applied Surface Science, vol. 255, No. 2, Nov. 15, 2008, pp. 526-533.

International Search Report issued Aug. 25, 2020 in International (PCT) Application No. PCT/JP2020/024938.

* cited by examiner

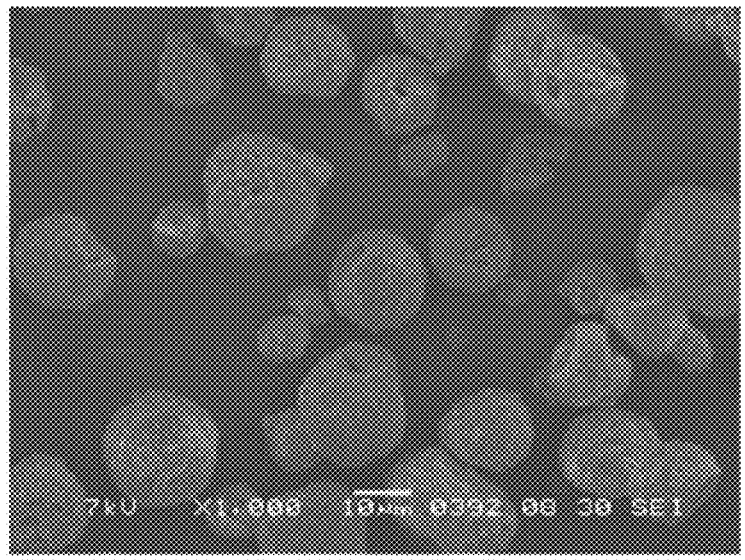
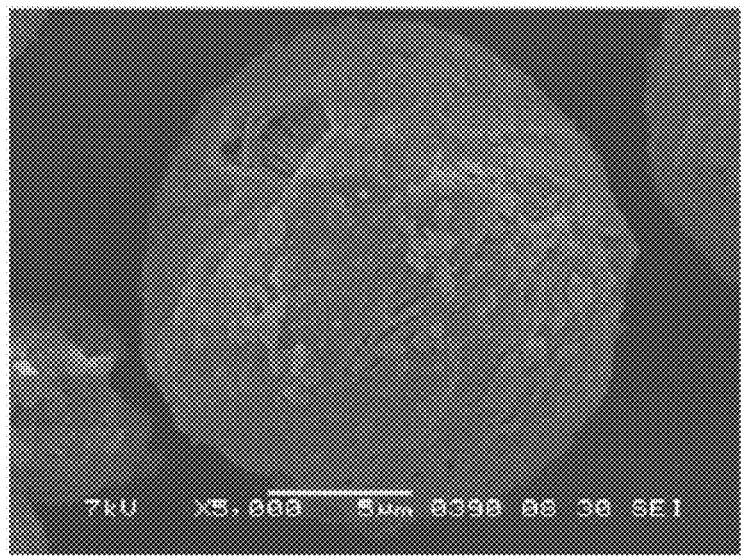

BIODEGRADABLE RESIN PARTICLES AND EXTERNAL PREPARATION INCLUDING THE SAME

CROSS-REFERENCE TO RELATED APPLICATIONS

This application is the U.S. National Phase under 35 U.S.C. § 371 of International Application PCT/JP2020/024938, filed Jun. 25, 2020, which claims priority to Japanese Patent Application No. JP 2019-121383, filed Jun. 28, 2019. The International Application was published under PCT Article 21(2) in a language other than English.

TECHNICAL FIELD

The present invention relates to biodegradable resin particles and an external preparation including the same.

BACKGROUND ART

Resin particles are used for modification and improvement of various materials, with the high specific surface area and a particle structure of the resin particles being utilized. Examples of major uses of resin particles include uses in cosmetic formulations, such as foundations, antiperspirants, and scrubbing agents; uses in various agents, such as matting agents for coating compositions, rheology modifying agents, anti-blocking agents, smoothing agents, light-diffusing agents, and agents for medical diagnosis and examination; and uses in additives for molded products of automotive materials, construction materials, and the like. Examples of the resin particles include urethane particles, acrylic particles, silicone particles, and polyethylene particles.

In this regard, as concerns over environmental issues have been growing in recent years, there is a demand for using a material derived from a non-petroleum raw material or using a biodegradable material in all fields that use a resin, to reduce environmental impact. For example, fields that use resin particles, such as fields of cosmetics and fields of coating compositions, are required to meet this demand.

Known methods for producing resin particles in which a biodegradable material is used include milling methods represented by cryomilling (PTL 1); and solvent dissolution-precipitation methods, such as methods in which a resin is dissolved in a solvent at a high temperature, and the resultant is cooled to cause precipitation, and methods in which a resin is dissolved in a solvent, and a poor solvent is subsequently added to cause precipitation (PTL 2).

CITATION LIST

Patent Literature

PTL 1: Japanese Unexamined Patent Application Publication No. 2017-2291
PTL 2: Japanese Unexamined Patent Application Publication No. 2016-102152

SUMMARY OF INVENTION

Technical Problem

Unfortunately, in instances where the resin particles of PTL 1 are used in an external preparation, such as a cosmetic, there are problems in that, for example, the resin particles do not have a spherical shape or a small particle diameter; therefore, further improvement is required in the resin particles in terms of spreadability on the skin. The resin particles of PTL 2 have a relatively spherical shape; however, there has been a problem in that the resin particles do not have a small particle diameter. In addition, there has been a problem in that since the particles have a porous surface, the particles are brittle and, therefore, have low stability.

An object of the present invention is to provide biodegradable resin particles and an external preparation including the same. The biodegradable resin particles have a small particle diameter and are excellent in terms of adhesion to the skin and smooth spreading on the skin in instances in which the biodegradable resin particles are applied to the skin.

Solution to Problem

The present invention relates to the following [1] and [2].

[1] Biodegradable resin particles including a polyhydroxy alkanoate; in the biodegradable resin particles, an amount of a Ca component present in the particles is 10 to 10,000 ppm, the biodegradable resin particles have a volume average particle diameter of 2 to 50 μm, the biodegradable resin particles have a BET specific surface area of 0.8 to 10 $m^2/g$, and the biodegradable resin particles have a linseed oil absorption of 50 to 300 ml/100 g.

[2] An external preparation including the biodegradable resin particles according to [1].

Advantageous Effects of Invention

With the present invention, biodegradable resin particles and an external preparation including the same are provided. The biodegradable resin particles have a small particle diameter and are excellent in terms of adhesion to the skin and smooth spreading on the skin in instances in which the biodegradable resin particles are applied to the skin.

BRIEF DESCRIPTION OF DRAWINGS

FIG. 1 is an SEM micrograph of biodegradable resin particles of Example 1.

DESCRIPTION OF EMBODIMENTS (Biodegradable Resin Particles)

Biodegradable resin particles of the present invention (hereinafter also referred to as "resin particles of the present invention") are biodegradable resin particles including a polyhydroxy alkanoate. The polyhydroxy alkanoate may be a polymer or a copolymer including one or more types of repeating units selected from the group consisting of 3-hydroxybutyrate repeating units, 3-hydroxyvalerate repeating units, 3-hydroxyhexanoate repeating units, and 3-hydroxyoctanoate repeating units. Among these, poly(3-hydroxybutyrate-co-3-hydroxyhexanoate), which is a copolymer of 3-hydroxybutyrate units and 3-hydroxyhexanoate units, poly(3-hydroxybutyrate-co-3-hydroxyoctanoate), which is a copolymer of 3-hydroxybutyrate units and 3-hydroxyoctanoate units, and poly(3-hydroxybutyrate-co-3-hydroxyhexanoate-co-3-hydroxyvalerate), which is a copolymer of 3-hydroxybutyrate units, 3-hydroxyhexanoate units, and 3-hydroxyvalerate units are preferable from the standpoint of providing ease of handling and a good sensory feel. Note that in the present invention, the "biodegradable resin particles including a polyhydroxy alkanoate" are resin particles formed essentially of a polyhydroxy alkanoate; in the particles, the presence of various components, such as a Ca component, 3-alkoxy-3-methyl-1-butanol, and 3-alkoxy-3-methyl-1-butyl acetate, is not excluded, that is, any of various components may be included.

The biodegradable resin particles of the present invention have a volume average particle diameter of 2 to 50 µm. If the volume average particle diameter is less than 2 µm, smoothness on the skin may be degraded. If the volume average particle diameter is greater than 50 µm, the feel tends to be poor in instances in which the biodegradable resin particles are used on the skin, for example, by being included in an external preparation. The volume average particle diameter is preferably within a range of 3 to 45 µm, more preferably within a range of 5 to 35 µm, even more preferably within a range of 8 to 30 µm, still more preferably within a range of 8 to 25 µm, and particularly preferably within a range of 8 to 20 µm. The volume average particle diameter is measured by using a method described later in the Examples section.

It is preferable that the biodegradable resin particles of the present invention have a coefficient of variation (CV value) of particle diameters of less than or equal to 45%, although this is not a limitation. When the coefficient of variation is less than or equal to 45%, not many coarse particles are present, and, therefore, a good feel is provided in instances in which the biodegradable resin particles are used in an external preparation. The coefficient of variation is more preferably less than or equal to 40% and even more preferably less than or equal to 35%.

The biodegradable resin particles of the present invention have a BET specific surface area of 0.8 to 10 m$^2$/g. If the specific surface area is less than 0.8 m$^2$/g, the particles have a high specific gravity and tend to settle, that is, the ease of handling during the preparation of an external preparation is reduced; therefore, such a specific surface area is not preferable. If the specific surface area is greater than 10 m$^2$/g, the biodegradable resin particles have large surface irregularities or a porous shape, and, therefore, the particles have low strength, which results in a reduced storage stability; therefore, such a specific surface area is not preferable. The specific surface area is preferably within a range of 0.9 to 8 m$^2$/g and more preferably within a range of 1 to 5 m$^2$/g. The BET specific surface area is measured by using a method described later in the Examples section.

The biodegradable resin particles of the present invention have a linseed oil absorption of 50 to 300 ml/100 g. If the linseed oil absorption is less than 50 ml/100 g, smoothness on the skin may be reduced. If the oil absorption is greater than 300 ml/100 g, viscosity tends to increase during the preparation of a liquid foundation or an external preparation, that is, the ease of handling is significantly reduced; therefore, such an oil absorption is not preferable. The oil absorption is preferably within a range of 55 to 250 ml/100 g and more preferably within a range of 60 to 200 ml/100 g. The linseed oil absorption is measured by using a method described later in the Examples section.

In the biodegradable resin particles of the present invention, a Ca component present in the particles is in an amount of 10 to 10,000 ppm. The presence of a Ca component in an amount greater than or equal to 10 ppm improves affinity for lipophilic substances, and, therefore, lumps are unlikely to form during the preparation of an external preparation; as a result, good smoothness on the skin tends to be achieved. Furthermore, since the Ca component is present in an amount less than or equal to 10,000 ppm, the release of the Ca component from the resin particles is effectively inhibited. If the Ca component is present in an amount greater than 10,000 ppm, adhesion to the skin tends to be reduced due to an influence of a hardness of the Ca component, in instances in which the biodegradable resin particles are used on the skin, for example, by being included in an external preparation; therefore, such an amount of the Ca component is not preferable. The amount of the Ca component is preferably within a range of 20 to 5,000 ppm and more preferably within a range of 30 to 500 ppm. The amount of the Ca component is measured by using a method described later in the Examples section.

A 10% compression strength of the biodegradable resin particles of the present invention is not particularly limited and may be greater than or equal to 0.5 MPa, which is preferable from the standpoint of achieving good smoothness on the skin; more preferably, the 10% compression strength is greater than or equal to 0.7 MPa, and even more preferably, greater than or equal to 1 MPa. Furthermore, the 10% compression strength may be less than or equal to 10 MPa, which is preferable from the standpoint of providing a soft feel; more preferably, the 10% compression strength is less than or equal to 8 MPa, and even more preferably, less than or equal to 6 MPa. Any combination of these ranges may be employed. The compression strength is measured by using a method described later in the Examples section.

The biodegradable resin particles of the present invention may have a particle surface coated with a dispersion stabilizing agent, and the dispersion stabilizing agent may be removed as necessary. A coating amount of the dispersion stabilizing agent can be estimated from an ash content, which is an ash content after the resin particles are heated at 750° C. for 30 minutes. In instances where an ash content of 0.01 to 3% is achieved by the removal, the release of the dispersion stabilizing agent from the particles is effectively inhibited. The ash content is measured by using a method described later in the Examples section.

Examples of the dispersion stabilizing agent include, but are not limited to, poorly water-soluble inorganic compounds, such as calcium carbonate and calcium phosphate. Among these, calcium carbonate is preferable in terms of ease of removing the dispersion stabilizing agent. In particular, calcium carbonate surface-treated with a silane coupling agent is preferable because such calcium carbonate has high affinity for biodegradable resins and excellent dispersion stability, and a particle diameter thereof can be easily controlled. The particle diameter of the dispersion stabilizing agent is not particularly limited. From the standpoint of a high specific surface area, it is preferable that the dispersion stabilizing agent have a small primary particle diameter. An average primary particle diameter of the dispersion stabilizing agent is preferably 10 to 1000 nm, more preferably 10 to 500 nm, and even more preferably 10 to 100 nm.

The biodegradable resin particles of the present invention may further contain at least one of 3-alkoxy-3-methyl-1-butanol and 3-alkoxy-3-methyl-1-butyl acetate (in each of which the alkoxy group has 1 to 5 carbon atoms). The inclusion of at least one of the substances improves affinity for hydrophilic substances and lipophilic substances. A content thereof may be 0.010 to 0.500 mass %, which is preferable in terms of ease of handling for dealing with the biodegradable resin particles as a powder; more preferably, the content is 0.020 to 0.100 mass %.

(Method for Producing Biodegradable Resin Particles)

Methods for producing the biodegradable resin particles of the present invention are not particularly limited. An example of the methods is a production method including the following steps (1) to (4).

(1) A step (emulsification and dispersion step) of emulsifying and dispersing a polyhydroxy alkanoate resin, which is used as a biodegradable resin, in the presence of a solvent, water, and a dispersion stabilizing agent at a temperature within a range of $T_{max} \pm 15°$ C., where the solvent contains at least one of 3-alkoxy-3-methyl-1-butanol and 3-alkoxy-3-methyl-1-butyl acetate (in each of which the alkoxy group has 1 to 5 carbon atoms), and $T_{max}$ is a peak temperature that is a maximum melting point of the resin as measured by DSC (2) A step (cooling and particle production step) of cooling the resultant and, accordingly, obtaining a dispersion of biodegradable resin particles having a particle surface coated with the dispersion stabilizing agent (3) A step (dispersion stabilizing agent removal step) of removing the coated dispersion stabilizing agent and, accordingly, obtaining a dispersion of biodegradable resin particles (4) A step (powder production step) of subjecting the particles obtained in (2) or (3) to filtering, washing, dehydration, drying, and classification and, accordingly, obtaining a powder of the biodegradable resin particles In the production method described above, an alcohol solvent that is safe is used while the use of organic solvents having skin irritation (e.g., xylene, toluene, n-methylpyrrolidone, chloroform, methylene chloride, dioxolane, THF, and the like) that are often used in typical micronizing processes for biodegradable resins is eliminated, and biodegradable resin particles that are spherical, have a small particle diameter, and have a narrow particle size distribution can be produced. Furthermore, 3-alkoxy-3-methyl-1-butanol and/or 3-alkoxy-3-methyl-1-butyl acetate are biodegradable and have low skin irritation, and, therefore, in uses in applications such as those for cosmetics, adverse effects that may be caused by a residual solvent can be inhibited. In addition, 3-alkoxy-3-methyl-1-butanol and/or 3-alkoxy-3-methyl-1-butyl acetate dissolve or plasticize biodegradable resins at high temperatures but do not dissolve biodegradable resins at ambient temperature, and, therefore, these alcoholic solvents can be easily recycled, which is industrially advantageous. The biodegradable resin particles prepared by this production method have an effect of having an excellent oil absorption property compared with particles prepared by a different production method.

(a) Emulsification and Dispersion Step

The solvent includes 3-alkoxy-3-methyl-1-butanol and/or 3-alkoxy-3-methyl-1-butyl acetate (hereinafter also referred to as a "specific solvent"). A proportion of the specific solvent in the solvent may be within a range of 10 to 90%, which is preferable from the standpoint of the oil absorption property and particle production; more preferably, the proportion is within a range of 20 to 80%, and even more preferably, within a range of 30 to 70%. Examples of solvents that may be used in addition to the specific solvent include lower alcohols, such as methanol and ethanol, and acetic acid ester-based solvents, such as ethyl acetate and butyl acetate. The specific solvent may be a solvent that is marketed by Kuraray Co., Ltd. under the trade name of Solfit. The 3-alkoxy-3-methyl-1-butanol can be produced, for example, by using a method described in International Publication No. WO2013/146370. The alkoxy groups in the specific solvent each independently have 1 to 5 carbon atoms. If the alkoxy groups have greater than 5 carbon atoms, solubility may be degraded. Specific examples of the alkoxy group include methoxy groups, ethoxy groups, propoxy groups, butoxy groups, and pentyloxy groups. The propoxy groups, the butoxy groups, and the pentyloxy groups include not only those having a linear structure but also possible structural isomers. It is preferable that the alkoxy group be a methoxy group, an ethoxy group, or a propoxy group. An amount of use of the solvent, per 100 parts by mass of the biodegradable resin, may be 100 to 1200 parts by mass, which is preferable from the standpoint of sufficiently performing stirring and mixing and from the standpoint of productivity; more preferably, the amount of use is 100 to 800 parts by mass, and even more preferably, 100 to 400 parts by mass.

The dispersion stabilizing agent may be any of the dispersion stabilizing agents mentioned above. In instances where the primary particle diameter is submicron or less, many of the particles are in the form of agglomerates when the dispersion stabilizing agent is in the form of a powder, and, therefore, it is preferable that the dispersion stabilizing agent be subjected to a deagglomeration process. The method for the deagglomeration is not particularly limited and may be one that uses, for instance, a wet ball mill or bead mill, which is preferable from the standpoint of preventing reagglomeration. It is preferable, from the standpoint of preventing reagglomeration, that the dispersion stabilizing agent be stored in the form of a solvent dispersion. A solids concentration of the solvent dispersion is not particularly limited and may be 3% to 20%, which is preferable from the standpoints of inhibiting settling and agglomeration and preventing deagglomeration failure; more preferably, the solids concentration is 4 to 18%, and even more preferably, 5 to 15%.

Furthermore, a surfactant, such as an anionic surfactant, may also be used, in addition to the dispersion stabilizing agent. An amount of addition of the surfactant may be 0.01 to 0.5 parts by mass per 100 parts by mass of water, for example.

To cause a shear force sufficient to form an emulsion during the stirring with heating, the mixing may be performed by using a commonly known method, such as a liquid-phase stirring method that uses a stirring blade, a mixing method that uses a homogenizer, or an ultrasonic irradiation method. The speed and time for the stirring is to be appropriately selected such that the biodegradable resin is uniformly dispersed in the solvent. Typically, the stirring with heating is performed under pressure.

(b) Cooling and Particle Production Step

After the stirring with heating, the solvent containing the biodegradable resin is cooled. It is preferable that the cooling from a temperature for the stirring with heating to a cooling temperature be performed gradually. Specifically, it is preferable that the cooling be performed at a rate of 0.5 to 5.0° C./minute. Furthermore, it is preferable that the cooling be performed with stirring. The stirring speed may be within a range similar to that of the stirring speed of the stirring with heating.

(c) Dispersion Stabilizing Agent Removal Step and Powder Production Step

After the cooling, the biodegradable resin particles in the solvent are subjected to filtration, washing, dehydration, and drying, to be extracted from the solvent. In instances where biodegradable resin particles not coated with the dispersion stabilizing agent are to be obtained, a step of removing the dispersion stabilizing agent with acid or the like is to be additionally performed before the filtration step mentioned above. Preferably, the decomposition of the dispersion stabilizing agent may be performed as follows from the standpoint of the spreadability on the skin and inhibition of hydrolysis: acid is added in an amount 1.05 to 1.50 times the necessary moles, or more preferably 1.05 to 1.20 times the necessary moles, so as to avoid producing strong acid, thereafter, stirring is performed at 40° C. or less, and then filtration and washing are performed within 24 hours, or more preferably within 12 hours. The drying can be performed by using a reduced-pressure drying method or a spray drying method. The dried biodegradable resin particles are to be subjected to classification, and, accordingly, the biodegradable resin particles of the present invention can be obtained. Examples of methods for the classification include air classification and screen classification. The air classification is a method that utilizes an air stream to classify particles. The screen classification is a method in which biodegradable resin particles are fed onto a screen, and the screen is vibrated, so that the biodegradable resin particles on the screen can be separated into particles that pass through the screen mesh and particles that do not pass through the screen mesh. It is preferable that the classification be performed in a dehumidified air atmosphere so that the biodegradable resin particles do not absorb moisture from the air. Specifically, the classification may be performed preferably in an atmosphere with a relative air humidity of 30% or less, and more preferably in an atmosphere with a relative air humidity of 20% or less. It is preferable that after production, the biodegradable resin particles obtained as described above be hermetically enclosed in a low-moisture-permeability packaging material and stored as a packaged article, so that the biodegradable resin particles do not absorb moisture from the air.

(External Preparation)

The biodegradable resin particles of the present invention can be suitably used, for example, by being included in an external preparation, such as a cosmetic or a quasi-drug. Examples of the cosmetic include powder foundations, milky lotions, and liquid foundations. Examples of the quasi-drug include scrubs.

A content of the biodegradable resin particles of the present invention in a cosmetic of the present invention may be appropriately set in accordance with the type of the cosmetic. The content may be greater than or equal to 0.1 mass %, which is preferable from the standpoint of enabling a desired effect to be produced; more preferably, the content is greater than or equal to 0.5 mass %, and even more preferably, greater than or equal to 1 mass %. Furthermore, the content may be less than or equal to 50 mass %, which is preferable from the standpoint of production cost, stability, and a good feel; more preferably, the content is less than or equal to 30 mass %. Any combination of these ranges may be employed.

Examples of the cosmetic of the present invention include, but are not limited to, make-up cosmetics, such as white makeup powders, face powders (e.g., loose powders and pressed powders), foundations (e.g., powder foundations, liquid foundations, and emulsion-type foundations), lipsticks, lip balms, blushers, cosmetics for eyes and eyebrows, and nail polishes; cleansing cosmetics, such as soaps, body shampoos, facial cleansing creams, scrub facial cleansers, and dentifrices; lotions, such as pre-shave lotions and body lotions; formulations for external use for bodies, such as body powders and baby powders; skin care cosmetics, such as skin lotions, creams, and milky lotions (cosmetic milky lotions); sunscreen cosmetics; sun tanning agents; antiperspirants (e.g., liquid antiperspirants, solid antiperspirants, and cream antiperspirants); packs; hair-washing cosmetics; hair colors; hair dressings; fragrant cosmetics; bath preparations; and shaving creams. In particular, skin care cosmetics, cleansing cosmetics, sunscreen cosmetics, and the like are preferable from the standpoint of reducing environmental impact.

The cosmetics of the present invention may include a commonly used base compound or an additive in accordance with a purpose, to an extent that does not impair the effects of the present invention. Examples of the base compound or additive include water, lower alcohols (alcohols having 5 or fewer carbon atoms), fats and oils, waxes, hydrocarbons, higher fatty acids, higher alcohols, sterols, fatty acid esters, metal soaps, moisturizing agents, surfactants, polymers, coloring materials, flavoring agents, clay minerals, antiseptic and bactericidal agents, anti-inflammatory agents, antioxidants, UV absorbers, organic-inorganic composite particles, pH adjusting agents (e.g., triethanolamine), specially formulated additives, and pharmaceutical active substances.

Specific examples of the fats and oils and the waxes include avocado oil, almond oil, olive oil, cacao butter, beef tallow, sesame oil, wheat germ oil, safflower oil, shea butter, turtle oil, camellia oil, persic oil, castor oil, grape seed oil, macadamia nut oil, mink oil, egg-yolk oil, Japan wax, coconut oil, rose hip oil, hydrogenated oil, silicone oil, orange roughy oil, carnauba wax, candelilla wax, spermaceti wax, jojoba oil, montan wax, beeswax, and lanolin.

Specific examples of the hydrocarbons include liquid paraffin, petrolatum, paraffin, ceresin, microcrystalline wax, and squalane.

Specific examples of the higher fatty acids include lauric acid, myristic acid, palmitic acid, stearic acid, oleic acid, behenic acid, undecylenic acid, oxystearic acid, linoleic acid, lanolin fatty acid, fatty acids having 11 or more carbon atoms, such as synthetic fatty acid.

Specific examples of the higher alcohols include alcohols having 6 or more carbon atoms, such as lauryl alcohol, cetyl alcohol, cetostearyl alcohol, stearyl alcohol, oleyl alcohol, behenyl alcohol, lanolin alcohol, hydrogenated lanolin alcohol, hexyldecanol, octyldecanol, isostearyl alcohol, jojoba alcohol, and decyltetradecanol.

Specific examples of the sterols include cholesterol, dihydrocholesterol, and phytocholesterol.

Specific examples of the fatty acid esters include linoleic acid esters, such as ethyl linoleate; lanolin fatty acid esters, such as isopropyl lanolate; lauric acid esters, such as hexyl laurate; myristic acid esters, such as isopropyl myristate, myristyl myristate, cetyl myristate, and octyldodecyl myristate; oleic acid esters, such as decyl oleate and octyldodecyl oleate; dimethyl octanoic acid esters, such as hexyldecyl dimethyloctanoate; isooctanoic acid esters, such as cetyl isooctanoate (cetyl 2-ethylhexanoate); isononanoic acid esters, such as ethylhexyl isononanoate, isononyl isononanoate, and isotridecyl isononanoate; palmitic acid esters, such as isopropyl palmitate, ethylhexyl palmitate, and decyl palmitate; glycerol trimyristate, glycerol tricaprylate/caprate, propylene glycol dioleate, glycerol triisostearate, glycerol triisooctanoate, cetyl lactate, myristyl lactate, diisostearyl malate, and cyclic alcohol fatty acid esters, such as cholesteryl isostearate and cholesteryl 12-hydroxystearate.

It is preferable that the oils, such as the fats and oils and the waxes, the hydrocarbons, the higher fatty acids, the higher alcohols, the sterols, and the fatty acid esters, be non-volatile oils. The oils are more preferably non-volatile oils having a viscosity of less than or equal to 550 mPa·s at 20° C., more preferably, non-volatile oils having a viscosity of 1 to 550 mPa·s at 20° C., and even more preferably, non-volatile oils having a viscosity of 5 to 550 mPa·s at 20° C. In cases where such a non-volatile oil is combined with the biodegradable resin particles of the present invention, the particles can be uniformly applied because of a high affinity for the oil; therefore, effects can be produced, such as a bright finish with a good texture after the application, excellent adhesion to the skin, smooth spreading on the skin, and excellent temporal stability. Suitable examples of the non-volatile oils having a viscosity of less than or equal to 550 mPa·s at 20° C. include liquid paraffin, squalane, olive oil, castor oil, jojoba oil, mink oil, macadamia nut oil, hexyl laurate, isopropyl myristate, octyldodecyl myristate, cetyl isooctanoate (cetyl 2-ethylhexanoate), ethylhexyl isononanoate, isononyl isononanoate, isotridecyl isononanoate, isopropyl palmitate, ethylhexyl palmitate, decyl palmitate, glycerol tricaprylate/caprate, glycerol triisostearate, and glycerol triisooctanoate. A content of the non-volatile oil in the cosmetic of the present invention may be 1 to 20 mass %, which is preferable from the standpoint of enabling the effects to be produced. In this specification, the "non-volatile oil" refers to an oil that remains on the skin for at least several hours at room temperature and atmospheric pressure and, in particular, has a vapor pressure of less than 0.13 Pa (0.01 mmHg).

Specific examples of the metal soaps include zinc laurate, zinc myristate, magnesium myristate, zinc palmitate, zinc stearate, aluminum stearate, calcium stearate, magnesium stearate, and zinc undecylenate.

Specific examples of the moisturizing agents include glycerol, propylene glycol, 1,3-butylene glycol, polyethylene glycol, sodium dl-pyrrolidonecarboxylate, sodium lactate, sorbitol, sodium hyaluronate, polyglycerol, xylitol, and maltitol.

Specific examples of the surfactants include anionic surfactants, such as higher fatty acid soaps, higher alcohol sulfuric acid esters, N-acyl glutamic acid salts, and phosphoric acid ester salts; cationic surfactants, such as amine salts and quaternary ammonium salts; amphoteric surfactants, such as betaine-type surfactants, amino acid-type surfactants, imidazoline-type surfactants, and lecithin; and nonionic surfactants, such as fatty acid monoglyceride, polyethylene glycol, propylene glycol fatty acid esters, sorbitan fatty acid esters, sucrose fatty acid esters, polyglycerol fatty acid esters, and ethylene oxide condensates.

Specific examples of the polymers include natural polymers, such as gum arabic, gum tragacanth, guar gum, locust bean gum, karaya gum, Irish moss, quince seed, gelatin, shellac, rosin, and casein; semi-synthetic polymers, such as sodium carboxymethyl cellulose, hydroxyethyl cellulose, methyl cellulose, ethyl cellulose, sodium alginate, ester gum, nitrocellulose, hydroxypropyl cellulose, and crystalline cellulose; and synthetic polymers, such as polyvinyl alcohol, polyvinylpyrrolidone, sodium polyacrylate, carboxyvinyl polymers, polyvinyl methyl ether, polyamide resins, silicone oils, and resin particles, such as nylon particles, poly(meth)acrylic acid ester particles (e.g., polymethylmethacrylate particles or the like), polystyrene particles, silicone-based particles, urethane particles, polyethylene particles, and silica particles.

Specific examples of the coloring materials include inorganic pigments, such as iron oxide (e.g., red iron oxide, yellow iron oxide, and black iron oxide), ultramarine blue, iron blue, chromium oxide, chromium hydroxide, carbon black, manganese violet, titanium oxide, zinc oxide, talc, kaolin, calcium carbonate, magnesium carbonate, mica, aluminum silicate, barium silicate, calcium silicate, magnesium silicate, silica, zeolite, barium sulfate, calcined calcium sulfate (calcined gypsum), calcium phosphate, hydroxyapatite, and ceramic powders; and tar dyes, such as azo-based dyes, nitro-based dyes, nitroso-based dyes, xanthene-based dyes, quinoline-based dyes, anthraquinone-based dyes, indigo-based dyes, triphenylmethane-based dyes, phthalocyanine-based dyes, and pyrene-based dyes.

Note that raw material powders of the polymers and raw material powders of the coloring materials or the like may be ones surface-treated in advance. As the method for the surface treatment, a known surface treatment technique may be used. Examples of the treatment technique include treatment with oil, such as a hydrocarbon oil, an ester oil, or lanolin; treatment with silicone, such as dimethylpolysiloxane, methylhydrogenpolysiloxane, or methylphenylpolysiloxane; treatment with a fluorinated compound, such as a perfluoroalkyl-group-containing ester, a perfluoroalkylsilane, a perfluoropolyether, or a perfluoroalkyl-group-containing polymer; treatment with a silane coupling agent, such as 3-methacryloxypropyl trimethoxysilane or 3-glycidoxypropyltrimethoxysilane; treatment with a titanium coupling agent, such as isopropyl triisostearoyl titanate or isopropyl tris(dioctylpyrophosphate) titanate; treatment with a metal soap; treatment with amino acid, such as acyl glutamic acid; treatment with lecithin, such as hydrogenated egg-yolk lecithin; treatment with collagen; treatment with polyethylene; moisturizing treatment; treatment with an inorganic compound; and mechanochemical treatment.

Specific examples of the flavoring agents include anisaldehyde, benzyl acetate, and geraniol.

Specific examples of the clay minerals include ingredients that have multiple functions, such as a function of an extender pigment and a function of an adsorbent, and examples of the ingredients include talc, mica, sericite, titanium sericite (sericite coated with titanium oxide), muscovite, and Veegum®, manufactured by Vanderbilt.

Specific examples of the antiseptic and bactericidal agents include methylparaben, ethylparaben, propylparaben, benzalkonium, and benzethonium.

Specific examples of the antioxidants include dibutylhydroxytoluene, butylhydroxyanisole, propyl gallate, and tocopherol.

Specific examples of the UV absorbers include inorganic absorbers, such as micronized titanium oxide, micronized zinc oxide, micronized cerium oxide, micronized iron oxide, and micronized zirconium oxide; and organic absorbers, such as benzoic acid-based absorbers, para-aminobenzoic acid-based absorbers, anthranilic acid-based absorbers, salicylic acid-based absorbers, cinnamic acid-based absorbers, benzophenone-based absorbers, and dibenzoylmethane-based absorbers.

Specific examples of the specially formulated additives include hormones, such as estradiol, estrone, ethinyl estradiol, cortisone, hydrocortisone, and prednisone; vitamins, such as vitamin A, vitamin B, vitamin C, and vitamin E; skin astringents, such as citric acid, tartaric acid, lactic acid, aluminum chloride, aluminum potassium sulfate, aluminum chlorohydroxy allantoinate, zinc p-phenol sulfonate, and zinc sulfate; hair growth stimulants, such as cantharides tincture, capsicum tincture, ginger tincture, swertia extract, garlic extract, hinokitiol, carpronium chloride, glyceride pentadecanoate, vitamin E, estrogen, and photosensitive elements; and whitening agents, such as magnesium L-ascorbyl phosphate and kojic acid.

EXAMPLES

Now, the present invention will be described in detail with reference to examples. Note that the examples are merely illustrative of the present invention and are not intended to limit the present invention.

<Measurement of Volume Average Particle Diameter>

The volume average particle diameter of the resin particles is to be measured by using a Coulter Multisizer™ 4e (manufactured by Beckman Coulter, Inc.). To carry out the measurement, an aperture calibrated in accordance with a user's manual is to be appropriately selected based on a size of the particles to be measured. The measurement sample to be used is a dispersion obtained as follows: 0.1 g of the resin particles is dispersed in 10 ml of a 0.1 mass % aqueous solution of a nonionic surfactant by using a touch mixer (Touch Mixer MT-31, manufactured by Yamato Scientific Co., Ltd.) and an ultrasonic cleaner (Ultrasonic Cleaner VS-150, manufactured by Velvo-clear Co., Ltd.). During the measurement, the contents of the beaker are to be gently stirred to such an extent that gas bubbles are not introduced, and 100,000 resin particles are to be measured. The volume average particle diameter of the resin particles is an arithmetic mean in a volume-based particle size distribution of the 100,000 particles.

The coefficient of variation (CV value) of particle diameters of the resin particles is to be calculated according to the following equation.

Coefficient of variation of particle diameters of resin particles=(standard deviation of volume-based particle size distribution of resin particles÷volume average particle diameter of resin particles)×100

<Method for Measuring BET Specific Surface Area>

The BET specific surface area of the resin particles was measured in accordance with the BET method (nitrogen adsorption method) described in JIS Z 8830:2001 (ISO 9277, 1st Ed). A BET nitrogen adsorption isotherm of target resin particles was measured by using an automated specific surface area/pore distribution analyzer Tristar II 3020, manufactured by Shimadzu Corporation, and, from the amount of nitrogen adsorbed, the specific surface area was calculated by using the multi-point BET method.

The measurement was carried out after a pretreatment was performed with a hot gas purge. In the measurement, nitrogen was used as the adsorbate, and a constant volume method was used under the condition of an adsorbate cross-sectional area of 0.162 nm². Specifically, the pretreatment was performed as follows: nitrogen purging was performed for 15 minutes while the vessel containing the resin particles was heated at 65° C., the vessel was then allowed to cool to room temperature, and subsequently, vacuum degassing was performed for 90 minutes while the vessel was heated at 65° C.

<Method for Measuring Linseed Oil Absorption>

The linseed oil absorption of the resin particles was measured by using a method modified from the measurement method of JIS K 5101-13-2:2004. Specifically, first-grade linseed oil was used instead of boiled linseed oil, and the criteria for determining whether the end point was reached were changed. Details of the measurement of the oil absorption are as follows.

(A) Device and Tools

Measurement plate: a flat and smooth glass plate with dimensions of 200 mm (length)×200 mm (width)×5 mm (thickness)

Palette knife (spatula): one with a steel or stainless steel blade and a handle

Analytical balance (weighing scale): one with 10 mg readability

Burette: one with 10-ml capacity, in accordance with JIS R 3505:1994

(B) Reagent: First-Grade Linseed Oil (Manufactured by Wako Pure Chemical Industries, Ltd.)

(C) Measurement Method (1) 1 g of the resin particles is placed on a middle portion of the measurement plate, and the first-grade linseed oil is slowly added dropwise from the burette to a middle of the resin particles, with four or five drops being added per operation. For each of the operations, the entire resin particles and first-grade linseed oil are thoroughly kneaded with a palette knife.

(2) The dropwise addition and kneading are repeated until the entire resin particles and first-grade linseed oil become a solid putty-like lump. Thereafter, the kneading is performed for each addition of a drop, and a point at which the addition of the last drop of the first-grade linseed oil causes the paste (the kneaded product of the resin particles and the first-grade linseed oil) to suddenly become soft and begin flowing is designated as the end point.

(3) Determination of Flowing

In an instance where the addition of the last drop of the first-grade linseed oil causes the paste to suddenly become soft, and the paste moves when the measurement plate is turned to an upright position, it is determined that the paste is fluid. In an instance where the paste does not move when the measurement plate is turned to an upright position, an additional drop of the first-grade linseed oil is to be added.

(4) When the end point has been reached, the amount of the first-grade linseed oil consumed is read.

(5) Each measurement run is to be completed within 7 to 15 minutes. If the measurement run lasts more than 15 minutes, the measurement is to be performed again, and the value obtained in the instance in which the measurement was completed within the specified time is to be employed.

(D) Calculation of Oil Absorption

The oil absorption per 100 g of the sample is calculated according to the following equation.

$$O=(V/m) \times 100$$

In the equation, 0 is the oil absorption (ml/100 g), m is the mass (g) of the resin particles, and V is the volume (ml) of the first-grade linseed oil consumed.

Note that the measurement was performed three times, and the linseed oil absorption was determined as an average of the measurements.

<Method for Measuring 10% Compression Strength>

The 10% compression strength (S10 strength) of the resin particles was measured under the following measurement conditions by using a micro compression testing machine MCTM-210, manufactured by Shimadzu Corporation). Specifically, a measurement sample was prepared by applying, to a mirror-finished SKS flat plate, a dispersion containing the resin particles dispersed in ethanol and then drying the resultant. Next, in an environment at a room temperature of 20° C. and a relative humidity of 50±20%, an individual microscopic resin particle (which was in a state in which no other resin particles were present at least within a range of a diameter of 100 μm) was selected by using an optical microscope of the MCTM-210, and a diameter of the selected resin particle was measured by using a particle diameter measurement cursor of the MCTM-210. The selected particle was one having a particle diameter close to the volume average particle diameter. A test indenter was moved down onto the top of the selected resin particle at a loading rate, which is described below; in this manner, a load was gradually applied to the resin particle until a maximum load of 9.81 mN was reached. By using the load at which the rate of change in the diameter of the resin particle reached 10% with respect to the pre-measured diameter, the compression strength was determined according to the following equation. For each of the resin particles, the measurement was performed six times, and an average of four of the results, excluding the results of the maximum value and the minimum value, was designated as the compression strength (S10 strength) associated with the time at which the rate of change reached 10%.

<Calculation Equation for Compression Strength>

Compression strength (Mpa)=2.8×load (N)/{π×(particle diameter (mm))²}

<Measurement Conditions for Compression Strength>

Test temperature: an ambient temperature (20° C.) and a relative humidity of 50±20%

Upper press indenter: a flat indenter (made of diamond) with a diameter of 50 μm (For particles with a diameter greater than 50 μm, a flat indenter with a diameter of 500 μm was used.)

Lower press plate: an SKS flat plate
Test type: a compression test (MODE1)
Test load: 9.81 mN
Loading rate: 0.732 mN/s <Method for Measuring Ash Content>

The ash content of the resin particles is to be measured by using the following method.

1.0 g of the resin particles was weighed, and subsequently, the weighed resin particles were combusted at 750° C. for 30 minutes in a microwave muffle furnace Phoenix (manufactured by CEM Corporation), and the mass (g) of the remaining residue was measured. The measured mass (g) of the residue was divided by the mass (1.0 g) of the pre-measurement particles, and the result was converted into percentage. Accordingly, an ignition residue content (mass %) was determined.

<Amount of Ca component>

The amount of a Ca component present in the resin particles was measured by using a multi-type ICP emission spectrometer (ICPE-9000, manufactured by Shimadzu Corporation).

Specifically, 1.0 g of the resin particles was accurately weighed into a crucible, and the accurately weighed resin particles were ashed by being heated at 450° C. for 3 hours by using an electric furnace (a muffle furnace STR-15K, manufactured by Isuzu Seisakusho Co., Ltd.). The ashed resin particles were dissolved in 2 ml of concentrated hydrochloric acid, and the solution was made up to a volume of 50 ml with ultrapure water to prepare a measurement sample. A measurement that used the multi-type ICP emission spectrometer was performed on the measurement sample under the following measurement conditions, to obtain the peak intensity of the wavelength of metal element Ca. Next, from the obtained peak intensity of the wavelength of metal element Ca, a concentration (μg/ml) of the metal element Ca in the measurement sample was determined based on a standard curve for quantification generated by the standard curve generation method described below. The determined concentration, C (μg/ml), of the metal element Ca, and the mass, W (g), of the accurately weighed resin particles, were substituted into the following equation to calculate an amount of the remaining metal in the resin particles.

Amount of remaining metal=(C(μg/ml)/W(g))×50 (ml)

<Measurement Conditions>
Measurement wavelength: Ca (183.801 nm)
Direction of observation: axial direction
High-frequency output: 1.20 kW
Carrier flow rate: 0.7 L/min
Plasma flow rate: 10.0 L/min
Auxiliary flow rate: 0.6 L/min
Exposure time: 30 seconds <Standard Curve Generation Method>

A standard solution for a standard curve (XSTC-13 (general-purpose mixture standard solution), manufactured by SPEX, the United States, in which 31 elements are mixed (base: 5% $HNO_3$), each in an amount of approximately 10 mg/l) was diluted with ultrapure water in a stepwise manner to prepare standard solutions of different concentrations, namely, 0 ppm (blank), 0.25 ppm, 1 ppm, 2.5 ppm, and 5 ppm. The measurement that used the multi-type ICP emission spectrometer was performed on the standard solutions of the respective concentrations under the measurement conditions described above, to obtain the peak intensities of the wavelengths of metal element Ca. For the metal element Ca, the peak intensities were plotted against the concentrations, and an approximation curve (straight line or quadratic curve) was determined by using the least squares method, and the determined approximation curve was used as a standard curve for quantification.

<Measurement of 3-methoxy-3-methyl-1-butanol Content>

A 3-methoxy-3-methyl-1-butanol content in the biodegradable resin particles was measured by using the following method. 0.2 g of the resin particles was accurately weighed into a 10-ml centrifuge tube, 5 ml of methanol was added and mixed therewith, and subsequently, the resultant was subjected to ultrasonic extraction for 15 minutes. Subsequently, centrifugation was performed at 3,500 rpm for 30 minutes. Subsequently, 20 μl of 1000 ppm toluene-d8 (solution in methanol), which served as an internal standard, was added to a 2-ml volumetric flask, and the flask was made up to volume with the supernatant liquid resulting from the centrifugation. The solution, the volume of which has been made up, was filtered through a 0.20-μm non-aqueous GL chromatodisc, manufactured by GL Sciences Inc. Accordingly, a sample was prepared, and the sample was subjected to a measurement that used the following instrument and conditions.

[GC/MS Measurement Conditions]
Measurement instruments: JMS-Q1000GC MkII mass spectrometer,
manufactured by JEOL Ltd., and 7890A gas chromatograph,
manufactured by Agilent Technologies
Column: ZB-1 capillary column (1.0 μm×0.25 mmφ×60 m),
manufactured by Phenomenex, Inc.

[GC Oven Heating Conditions]
Initial temperature: 40° C. (held for 3 minutes)
First phase heating rate: 15° C./min (up to 200° C.)
Second phase heating rate: 25° C./min (up to 250° C.)
Final temperature: 250° C. (held for 6.33 minutes)
Carrier gas: He
He flow rate: 1 ml/min
Injection port temperature: 250° C.
Interface temperature: 250° C.
Detector voltage: −900 V
Split ratio: 1/50
Ion source temperature: 250° C.
Ionization current: 300 uA
Ionization energy: 70 eV
Detection method: SIM mode (3-methoxy-3-methyl-1-butanol (m/z=41, 69), toluene-d8 (m/z=98, 100))

In a GC/MS chromatogram of the obtained extracted sample, the area of the peak corresponding to 3-methoxy-3-methyl-1-butanol was calculated as an area ratio relative to the area of the peak of the toluene-d8, which served as an internal standard, and the measured value was determined from a standard curve generated in advance and was designated as a 3-methoxy-3-methyl-1-butanol content in the biodegradable resin particles.

Production Example 1

To a 2-L ball mill pot made of quartz glass, 3,500 g of 5 mm zirconia beads, 100 g of silane coupling agent-treated calcium carbonate (Actifort700, manufactured by Shiraishi Calcium Kaisha, Ltd., a primary particle diameter of 20 nm), 450 g of ion-exchanged water, and 450 g of 3-methoxy-3-methyl-1-butanol (Solfit Fine Grade, manufactured by Kuraray Co., Ltd.) were added, and the resultant was mounted to a ball mill rotary stand and processed at a peripheral speed of 100 rpm for 24 hours. Accordingly, a dispersion of calcium carbonate was obtained.

Production Example 2

A dispersion of calcium carbonate was obtained as in Production Example 1, except that the 100 g of silane coupling agent-treated calcium carbonate (Actifort700, manufactured by Shiraishi Calcium Kaisha, Ltd., a primary particle diameter of 20 nm) was replaced with 100 g of silane coupling agent-treated calcium carbonate (RK53BR, manufactured by Shiraishi Calcium Kaisha, Ltd., a primary particle diameter of 150 nm).

Example 1

To a 2-L autoclave equipped with a stirring blade and a thermometer, 120 g of a copolymer resin of 3-hydroxyhexanoate and 3-hydroxybutyrate (DAN-01210, manufactured by Danimer Scientific, a melting point $T_{max}$ of 142° C.), which was used as a biodegradable resin, 486 g of 3-methoxy-3-methyl-1-butanol, which was used as a solvent, 486 g of ion-exchanged water, and 120 g of the dispersion of calcium carbonate obtained in Production Example 1, which was used as a dispersion stabilizing agent, were added, and heating was performed such that an internal temperature became 142° C., while the contents were stirred at a rotational speed of 600 rpm. After the internal temperature reached 142° C., the mixture was emulsified for 60 minutes. Subsequently, the resultant was cooled to 30° C. over a period of 1 hour while the stirring speed was maintained. Accordingly, a suspension was obtained. 50 g (1.14 times the necessary moles) of 20% hydrochloric acid was added to the obtained suspension, which was then stirred for 10 minutes to decompose the calcium carbonate. Subsequently, the biodegradable resin particles were separated by using a centrifuge (manufactured by Tanabe Willtec Inc), and the obtained biodegradable resin particles were washed with ion-exchanged water, which was in an amount 20 times the amount of addition of the resin. Next, the obtained biodegradable resin particles were dried for 20 hours under the conditions of 60° C. and a vacuum of 0.05 MPa. A classification device (Hi-Bolter NR300 (trade name), manufactured by Toyo Hitec Co., Ltd.), equipped with a 45-μm mesh screen, was prepared. The biodegradable resin particles were classified with the classification device in an air atmosphere with a relative humidity of 20%. The biodegradable resin particles, which were caught in the flow of air having a relative humidity of 20%, were caused to collide with the screen to remove particles that did not pass through the screen mesh. In this manner, particles having a large particle diameter were removed, and, accordingly, biodegradable resin particles were obtained.

Example 2

A suspension was obtained as in Example 1, except that the amount of the biodegradable resin was changed to 240 g; the amount of the 3-methoxy-3-methyl-1-butanol, which was used as a solvent, to 372 g; the amount of the ion-exchanged water to 372 g; and the amount of the dispersion of calcium carbonate obtained in Production Example 1, which was used as a dispersion stabilizing agent, to 240 g. A dispersion stabilizing agent removal step, a washing step, and a drying step were performed as in Example 1, except that 100 g (1.14 times the necessary moles) of 20% hydrochloric acid was added to the obtained suspension. A classification step was performed as in Example 1, except that the mesh screen was replaced with a 63-μm mesh screen, and, accordingly, a biodegradable resin particles were obtained.

Example 3

Biodegradable resin particles were obtained as in Example 1, except that the emulsification temperature was changed to 135° C.

Example 4

An emulsification and dispersion step, a dispersion stabilizing agent removal step, a washing step, and a drying step were performed as in Example 1, except that the amount of the 3-methoxy-3-methyl-1-butanol was changed to 702 g, and the amount of the ion-exchanged water to 270 g. A classification step was performed as in Example 1, except that the mesh screen was replaced with a 96-μm mesh screen, and, accordingly, a biodegradable resin particles were obtained.

Example 5

A dispersion stabilizing agent removal step, a washing step, and a drying step were performed as in Example 1, except that the amount of the 3-methoxy-3-methyl-1-butanol was changed to 162 g, and the amount of the ion-exchanged water to 810 g. A classification step was performed as in Example 1, except that the mesh screen was replaced with a 63-μm mesh screen, and, accordingly, biodegradable resin particles were obtained.

Example 6

A dispersion stabilizing agent removal step, a washing step, and a drying step were performed as in Example 1, except that the 120 g of the dispersion of calcium carbonate obtained in Production Example 1, which was used as a dispersion stabilizing agent, was replaced with 120 g of the dispersion of calcium carbonate obtained in Production Example 2, which was used as a dispersion stabilizing agent. A classification step was performed as in Example 1, except that the mesh screen was replaced with a 53-μm mesh screen, and, accordingly, biodegradable resin particles were obtained.

Example 7

A dispersion stabilizing agent removal step, a washing step, and a drying step were performed as in Example 1, except that the 120 g of the copolymer resin of 3-hydroxyhexanoate and 3-hydroxybutyrate (DAN-01210, manufactured by Danimer Scientific, a melting point $T_{max}$ of 142° C.) was replaced with 120 g of a copolymer resin of 3-hydroxyhexanoate, 3-hydroxybutyrate, and 3-hydroxyvalerate (DAN-02265, manufactured by Danimer Scientific, a melting point $T_{max}$ of 142° C.). A classification step was performed as in Example 1, except that the mesh screen was replaced with a 53-µm mesh screen, and, accordingly, biodegradable resin particles were obtained.

Example 8

Biodegradable resin particles were obtained as in Example 1, except that the rotational speed was changed to 1200 rpm.

Comparative Example 1

A dispersion stabilizing agent removal step, a washing step, and a drying step were performed as in Example 1, except that the emulsification temperature was changed to 120° C. A classification step was performed as in Example 1, except that the mesh screen was replaced with a 150-µm mesh screen, and, accordingly, biodegradable resin particles were obtained.

Comparative Example 2

A similar operation to that of Example 1 was performed except that the amount of the 3-methoxy-3-methyl-1-butanol was changed to 1026 g, and no ion-exchanged water was added. Consequently, the cooled slurry was in the form of a gel, which made deliquoring difficult, and as a result, extraction of particles was not achieved.

Comparative Example 3

A dispersion stabilizing agent removal step, a washing step, and a drying step were performed as in Example 1, except that no 3-methoxy-3-methyl-1-butanol was added, and 1026 g of ion-exchanged water was added. A classification step was performed as in Example 1, except that the mesh screen was replaced with a 150-µm mesh screen, and, accordingly, biodegradable resin particles were obtained.

Comparative Example 4

Biodegradable resin particles were obtained as in Example 6, except that no 20% hydrochloric acid was added.

Comparative Example 5

To a 2-L autoclave equipped with a stirring blade and a thermometer, 56 g of a copolymer resin of 3-hydroxybutyrate and 3-hydroxyhexanoate (Aonilex X131A, manufactured by Kaneka Corporation, a melting point $T_{max}$ of 137° C.), 40 g of hydroxypropyl cellulose, and 704 g of ethyl acetoacetate were added, and the contents were heated to 120° C. and stirred for 2 hours until the resin was completely dissolved. After the temperature of the system was reduced back to 70° C., 800 g of a 50 mass % aqueous solution of ethanol was added dropwise via pump over a period of 2 hours while the system was stirred, and after the dropwise addition, the system was stirred for 30 minutes while the temperature of 70° C. was maintained. Subsequently, the system was cooled to 30° C., and the resulting suspension was washed with filter paper and 400 g of ion-exchanged water. The separated solids were dried for 10 hours under the conditions of 80° C. and a vacuum of 0.05 MPa, and, accordingly, resin particles were obtained.

(Powder Characteristics Test)

The resin particles of Examples 1 to 8 and Comparative Examples 1, 3, 4, and 5 were evaluated by ten expert panelists for the feel (a dry feel and smoothness) imparted by the application of the resin particles to the skin. The evaluations were made as described below based on the number of people who answered that the feel was good. A rating of "⊙" was given when the number of people was 9 to 10, a rating of "○" when the number was 7 to 8, a rating of "Δ" when the number was 4 to 6, and a rating of "x" when the number was 3 or less.

(Preparation of Powder Foundation)

Mixtures including the respective resin particles of Examples 1 to 8 and Comparative Examples 1, 3, 4, and 5 were each prepared as follows: 15 parts by mass of the resin particles, 21 parts by mass of sericite, 51 parts by mass of muscovite, 0.6 parts by mass of red iron oxide, 1 part by mass of yellow iron oxide, and 0.1 parts by mass of black iron oxide were mixed together in a Henschel mixer. Also, a solution was prepared by mixing and dissolving 1 part by mass of sorbitan sesquioleate and 0.2 parts by mass of a preservative in 10 parts by mass of cetyl 2-ethylhexanoate. The mixture and the solution were homogeneously mixed together, subsequently, 0.1 parts by mass of a flavoring agent was added thereto and homogeneously mixed, and subsequently, the resultant was ground and passed through a sieve. Accordingly, a material for a foundation was prepared. The material for a foundation was pressed into a pan, and, accordingly, a powder foundation was prepared. The ten panelists applied and spread the obtained powder foundation on their wrists and evaluated the powder foundation for adhesion to the skin and smooth spreading on the skin, according to the following criteria. The results are shown in Table 1. Note that the values in the table are averages of the test results of the ten panelists.

5: Very good
4: Good
3: Moderately good
2: Not good
1: Poor

Tables 1 and 2 summarize types of raw materials used, amounts thereof, and the emulsification temperature, of Examples 1 to 8 and Comparative Examples 1 to 5; the volume average particle diameter, coefficient of variation, BET specific surface area, linseed oil absorption, 10% compression strength, ash content, amount of a Ca component, of the biodegradable resin particles obtained in Examples 1 to 8 and Comparative Examples 1 to 5; and sensory evaluations of adhesion and spreadability of the foundations in which the biodegradable resin particles obtained in Examples 1 to 8 and Comparative Examples 1 to 5 were included.

TABLE 1

|  |  | Example 1 | Example 2 | Example 3 | Example 4 | Example 5 | Example 6 | Example 7 | Example 8 |
|---|---|---|---|---|---|---|---|---|---|
| Resin | DAN-01210 (g) | 120 | 240 | 120 | 120 | 120 | 120 | — | 120 |
|  | DAN-02265 (g) | — | — | — | — | — | — | 120 | — |
| Solvent | 3-methoxy-3-methyl-1-butanol (g) | 486 | 372 | 486 | 702 | 162 | 486 | 486 | 486 |
| Water | Ion-exchanged water (g) | 486 | 372 | 486 | 270 | 810 | 486 | 486 | 486 |
| Dispersion stabilizing agent | Dispersion of calcium carbonate (g) | Production example 1 | Production example 1 | Production example 1 | Production example 1 | Production example 1 | Production example 2 | Production example 1 | Production example 1 |
|  |  | 120 | 240 | 120 | 120 | 120 | 120 | 120 | 120 |
| Emulsification temperature (° C.) |  | 142 | 142 | 135 | 142 | 142 | 142 | 142 | 142 |
| Volume average particle diameter (μm) |  | 17.72 | 33.38 | 17.22 | 39.14 | 32.82 | 25.71 | 24.21 | 12.80 |
| Coefficient of variation (%) |  | 30.7 | 33.1 | 34.7 | 38.5 | 37.6 | 37.2 | 31.2 | 28.4 |
| BET specific surface area ($m^2/g$) |  | 1.83 | 3.04 | 3.42 | 3.85 | 1.36 | 0.99 | 2.05 | 3.67 |
| Linseed oil absorption (ml/100 g) |  | 101 | 173 | 151 | 180 | 118 | 89 | 115 | 135 |
| 10% compression strength (MPa) |  | 3.60 | 0.71 | 1.55 | 0.80 | 2.18 | 5.80 | 3.81 | 3.46 |
| Ash content (%) |  | 0.24 | 0.35 | 0.29 | 0.31 | 0.22 | 0.26 | 0.24 | 0.27 |
| Amount of Ca component (ppm) |  | 155 | 172 | 86 | 232 | 145 | 135 | 162 | 189 |
| 3-methoxy-3-methyl-1-butanol content (mass %) |  | 0.089 | 0.122 | 0.051 | 0.250 | 0.081 | 0.092 | 0.095 | 0.065 |
| Evaluation of feel of powder |  | ⊙ | ○ | ⊙ | ○ | ○ | ⊙ | ⊙ | ⊙ |
| Foundation | Adhesion | 4.2 | 3.2 | 4.2 | 3.0 | 3.1 | 3.8 | 3.9 | 4.4 |
|  | Spreadability | 4.0 | 4.1 | 3.9 | 3.4 | 3.7 | 3.5 | 3.7 | 4.3 |

TABLE 2

|  |  | Comparative example 1 | Comparative example 2 | Comparative example 3 | Comparative example 4 | Comparative example 5 |
|---|---|---|---|---|---|---|
| Resin | DAN-01210 (g) | 120 | 120 | 120 | 120 |  |
| Solvent | 3-methoxy-3-methyl-1-butanol (g) | 486 | 1026 | — | 486 |  |
| Water | Ion-exchanged water (g) | 486 | — | 1026 | 486 |  |
| Dispersion stabilizing agent | Dispersion of calcium carbonate (g) | Production example 1 | Production example 1 | Production example 1 | Production example 2 |  |
|  |  | 120 | 120 | 120 | 120 |  |
| Emulsification temperature (° C.) |  | 120 | 142 | 142 | 142 |  |
| Volume average particle diameter (μm) |  | 73.41 | Could not be obtained as particles | 68.26 | 27.25 | 54.23 |
| Coefficient of variation (%) |  | 50.8 |  | 46.8 | 36.2 | 50.6 |
| BET specific surface area ($m^2/g$) |  | 1.02 |  | 0.98 | 1.69 | 15.20 |
| Linseed oil absorption (ml/100 g) |  | 56 |  | 48 | 98 | 378 |
| 10% compression strength (MPa) |  | 2.01 |  | 1.53 | 7.80 | 0.32 |
| Ash content (%) |  | 0.22 |  | 0.22 | 5.17 | 0.01 |
| Amount of Ca component (ppm) |  | 212 |  | 155 | 48500 | Not detected |
| 3-methoxy-3-methyl-1-butanol content (mass %) |  | 0.138 |  | Not detected | 0.112 | Not detected |
| Evaluation of feel of powder |  | X |  | X | Δ | X |
| Foundation | Adhesion | 2.2 |  | 2.1 | 2.5 | 2.3 |
|  | Spreadability | 3.6 |  | 3.4 | 3.5 | 2.2 |

As described, in Comparative Example 1, in which emulsification and dispersion were not carried out at a temperature within the range of $T_{max} \pm 15°$ C., where $T_{max}$ was the peak temperature that was a maximum melting point of the resin as measured by DSC, the resulting resin particles were coarse, that is, resin particles having the target volume average particle diameter could not be obtained. In Comparative Example 2, in which 3-alkoxy-3-methyl-1-butanol and/or 3-alkoxy-3-methyl-1-butyl acetate (in each of which the alkoxy group has 1 to 5 carbon atoms) were exclusively used, the resin was excessively plasticized and became a gel, and, consequently, extraction of particles was not achieved. In Comparative Example 3, in which water was exclusively used, the resin was not plasticized, and, therefore, the resulting particles were coarse, that is, resin particles having the target volume average particle diameter could not be obtained. Furthermore, in Comparative Example 4, the removal of the Ca component was not performed, and as a result, adhesion to the skin was poor because an excessive amount of Ca remained. In Comparative Example 5, the particles had a diameter greater than the target volume average diameter, and, therefore, the particles were porous and brittle; as a result, the BET specific surface area and the linseed oil absorption were higher than the claimed ranges, that is, target particles could not be obtained. In contrast, in Examples 1 to 8, resin particles having the target volume average particle diameter were obtained. Furthermore, as described, the biodegradable resin particles of Examples 1 to 8, which had a small particle diameter and, therefore, were excellent in terms of adhesion to the skin and smooth spreading on the skin and had a particular strength, enabled realization of excellent adhesion to the skin, spreadability on the skin, and smoothness on the skin, as compared with those of Comparative Examples 1, 3, 4, and 5, which had a large particle diameter, in the instance in which the biodegradable resin particles were used in a powder foundation.

(Preparation of Solid Face Powder Cosmetic)

10 parts by mass of the biodegradable resin particles of Example 1, 70 parts by mass of talc, 5.5 parts by mass of titanium dioxide, and a pigment were thoroughly mixed together in a kneader (a powder portion). 1 part by mass of triethanolamine was added to 50 parts by mass of purified water, and the resultant was held at 70° C. (an aqueous phase). 1.5 parts by mass of stearic acid, 5 parts by mass of lanolin, 5 parts by mass of squalane, and 2 parts by mass of sorbitan sesquioleate were mixed together and then dissolved with heating and held at 70° C. (an oil phase). The oil phase was added to the aqueous phase, and the resultant was homogeneously emulsified with a homomixer. The powder portion was added to the emulsified product, and the resultant was kneaded in a kneader. Subsequently, moisture was evaporated from the kneaded product, and the kneaded product was then ground in a grinding mill. In addition, a flavoring agent was uniformly sprayed onto the ground product while the ground product was thoroughly stirred, and the resultant was pressed. Accordingly, a solid face powder cosmetic was obtained. The obtained solid face powder cosmetic enabled realization of excellent adhesion to the skin, spreadability on the skin, and smoothness on the skin.

(Preparation of Loose Powder)

5 parts by mass of the biodegradable resin particles of Example 1, 74.6 parts by mass of talc, 12 parts by mass of synthetic phlogopite, 5 parts by mass of zinc laurate, 3 parts by mass of lauroyl lysine, and 0.4 parts by mass of iron oxide were homogeneously mixed together in a Henschel mixer. Accordingly, a loose powder was obtained. The obtained loose powder enabled realization of excellent adhesion to the skin, spreadability on the skin, and smoothness on the skin.

(Preparation of Liquid Foundation)

5 parts by mass of the biodegradable resin particles of Example 1, 11.2 parts by mass of titanium dioxide, 0.3 parts by mass of red iron oxide, 2.2 parts by mass of yellow iron oxide, and 0.2 parts by mass of black iron oxide were mixed together in a kneader (a powder portion). 5 parts by mass of isotridecyl isononanoate, 0.25 parts by mass of propylparaben, 3.5 parts by mass of dimethicone/PEG-10/15 crosspolymer, 2 parts by mass of PEG-9 polydimethylsiloxyethyl dimethicone, 20.1 parts by mass of cyclopentasiloxane, 2 parts by mass of ethylhexyl methoxycinnamate, and 2 parts by mass of disteardimonium hectorite were mixed together and then dissolved with heating at 70° C. (an oil phase). 5 parts by mass of glycerol, 0.5 parts by mass of sodium chloride, 0.12 parts by mass of sodium dehydroacetate, 0.12 parts by mass of methylparaben, and 0.1 parts by mass of phenoxyethanol were added to 40.41 parts by mass of purified water and were dissolved with heating at 70° C. (an aqueous phase). The powder portion was added to the oil phase, and the powder was homogeneously dispersed with a homomixer. Subsequently, the aqueous phase was added thereto, the resultant was homogeneously emulsified and dispersed with the homomixer, and subsequently, the resultant was cooled with stirring. Accordingly, a liquid foundation was obtained. The obtained liquid foundation enabled realization of excellent adhesion to the skin, spreadability on the skin, and smoothness on the skin.

(Preparation of Pressed Powder)

8 parts by mass of the biodegradable resin particles of Example 1, 60.8 parts by mass of talc, 20 parts by mass of mica, 1.9 parts by mass of titanium dioxide, 0.14 parts by mass of red iron oxide, 0.8 parts by mass of yellow iron oxide, and 0.1 parts by mass of black iron oxide were mixed together in a Henschel mixer. Accordingly, a mixture was prepared (a powder portion). 4 parts by mass of squalane, 2 parts by mass of zinc laurate, 2 parts by mass of diisostearyl malate, 0.1 parts by mass of butyl paraben, 0.1 parts by mass of methyl paraben, 0.05 parts by mass of aluminum hydroxide, and 0.01 parts by mass of tocopherol were mixed together and then dissolved with heating at 70° C. (an oil phase). The oil phase was added to the powder portion and homogeneously mixed. Subsequently, the resultant was ground and passed through a sieve, and the resultant was pressed. Accordingly, a pressed powder was prepared.

The obtained pressed powder enabled realization of excellent adhesion to the skin, spreadability on the skin, and smoothness on the skin.

(Preparation of Eye Shadow)

5 parts by mass of the biodegradable resin particles of Example 1, 44.1 parts by mass of talc, 20 parts by mass of mica, 10 parts by mass of mica coated with titanium dioxide, 8 parts by mass of lauroyl lysine, 2 parts by mass of zinc laurate, 0.5 parts by mass of D&C Red No. 7, and 0.4 parts by mass of FD&C Yellow No. 6 were mixed together in a kneader (a powder portion). 2 parts by mass of dimethicone and 2 parts by mass of sorbitan sesquioleate were added to 6 parts by mass of mineral oil and dissolved with heating (an oil phase). The oil phase was added to the powder portion, the resultant was kneaded in a kneader, and subsequently, the kneaded product was pressed. Accordingly, an eye shadow was obtained. The obtained eye shadow enabled realization of excellent adhesion to the skin, spreadability on the skin, and smoothness on the skin.

(Preparation of Skin Cream)

13 parts by mass of glycerol, 1 part by mass of decaglyceryl monostearate, 0.5 parts by mass of decaglyceryl monolaurate, 1 part by mass of glyceryl monostearate, 2 parts by mass of stearyl alcohol, 3 parts by mass of glyceryl tri (caprylate/caprate), 2 parts by mass of meadowfoam oil, 2 parts by mass of jojoba oil, 0.1 parts by mass of di(phytosteryl/octyldodecyl) lauroyl glutamate, 3 parts by mass of dimethicone, and 3 parts by mass of cyclopentasiloxane were dissolved together with heating at 70° C. (an oil phase). 0.2 parts by mass of acrylates/C10-30 alkyl acrylate crosspolymer, 0.1 parts by mass of hydroxypropylmethyl cellulose, 0.05 parts by mass of disodium edetate, 0.01 parts by mass of sodium hyaluronate, 0.3 parts by mass of phenoxyethanol, 4 parts by mass of 1,3-butylene glycol, 0.1 parts by mass of sodium pyrrolidone carboxylate, and 63.1 parts by mass of purified water were dissolved together with heating at 70° C. (an aqueous phase). 1 part by mass of the biodegradable resin particles of Example 1 was added to the oil phase, the aqueous phase was then added thereto while the biodegradable resin particles were dispersed with a homomixer, and, accordingly, a homogeneous emulsified product was obtained. 0.5 mass of a 10% aqueous sodium hydroxide solution was added to the emulsified product, and the resultant was cooled to room temperature while being stirred with a disper. Accordingly, a skin cream was obtained. The obtained skin cream enabled realization of excellent adhesion to the skin, spreadability on the skin, and smoothness on the skin.

(Preparation of Body Lotion)

3 parts by mass of the biodegradable resin particles of Example 1, 50 parts by mass of ethanol, 0.1 parts by mass of glycyrrhizic acid, 0.5 parts by mass of a flavoring agent, and 46.4 parts by mass of purified water were thoroughly mixed together in a mixer. Accordingly, a body lotion was obtained. The obtained body lotion enabled realization of spreadability and smoothness for application to the skin.

(Preparation of Sunscreen Cream)

3 parts by mass of the biodegradable resin particles of Example 1, 7 parts by mass of dimethicone, 1 part by mass of Polysilicone-13, 1 part by mass of PEG-10 dimethicone, and 1.5 parts by mass of titanium oxide were stirred at room temperature for 1 hour (an oil phase A). 8.5 parts by mass of dimethicone, 4 parts by mass of cyclopentasiloxane, 1 part by mass of Polysilicone-13, and 10 parts by mass of zinc oxide were stirred at room temperature for 1 hour (an oil phase B). 10.5 parts by mass of 2-ethylhexyl-p-methoxycinnamate, 2.7 parts by mass of bis-ethylhexyloxyphenol methoxyphenyl triazine, 8.4 parts by mass of dimethicone, 2.5 parts by mass of ethylhexyl isononanoate, 2.5 parts by mass of squalane, 0.2 parts by mass of stearic acid, 2.5 parts by mass of talc, and 1 part by mass of quaternium-90 bentonite were dissolved with heating at 80° C. (an oil phase C). The oil phase A was added to the oil phase C, and subsequently, the oil phase B was added thereto, and these were mixed together with stirring at 80° C. 0.2 parts by mass of phenoxyethanol, 0.1 parts by mass of sodium metabisulfite, 3 parts by mass of 1,3-butylene glycol, 1 part by mass of glycerol, 0.5 parts by mass of PEG/PPG/polybutylene glycol-8/5/3 glycerol, and 27.9 parts by mass of purified water had been dissolved with heating at 80° C. in advance, and the entire oil phases were added thereto. The resultant was homogeneously emulsified and dispersed with a homomixer, and subsequently, the resultant was cooled with stirring. Accordingly, a sunscreen cream was obtained. The obtained sunscreen cream enabled realization of excellent adhesion to the skin, spreadability on the skin, and smoothness on the skin.

(Preparation of Lipstick)

10 parts by mass of the biodegradable resin particles of Example 1, 3 parts by mass of titanium dioxide, 0.5 parts by mass of D&C Red No. 7, and 2 parts by mass of D&C Red No. 11 were added to 15 parts by mass of liquid paraffin and thoroughly mixed together in a roller (a pigment portion). 0.05 parts by mass of D&C Red No. 21 was dissolved in 11.45 parts by mass of butyl stearate (a dye portion). 12 parts by mass of ceresin, 8 parts by mass of beeswax, 5 parts by mass of cetyl alcohol, 4 parts by mass of spermaceti wax, 1 part by mass of carnauba wax, 6 parts by mass of liquid paraffin, 20 parts by mass of liquid lanolin, 2 parts by mass of sorbitan sesquioleate, a flavoring agent, and an antioxidant were mixed together and then dissolved with heating. Subsequently, the pigment portion and the dye portion were added thereto and homogeneously dispersed with a homomixer. After dispersion, the resultant was poured into a mold and rapidly cooled. Accordingly, a lipstick having a stick shape was obtained. The obtained lipstick enabled realization of excellent adhesion and excellent spreadability and smoothness for application.

INDUSTRIAL APPLICABILITY

The resin particles of the present invention can be suitably used by being included in an external preparation, such as a cosmetic or a quasi-drug.

The invention claimed is:

1. Biodegradable resin particles comprising a polyhydroxy alkanoate, wherein
    an amount of a Ca component present in the particles is 10 to 10,000 ppm,
    the biodegradable resin particles have a volume average particle diameter of 2 to 50 μm,
    the biodegradable resin particles have a BET specific surface area of 0.8 to 10 m²/g, and
    the biodegradable resin particles have a linseed oil absorption of 50 to 300 ml/100 g.

2. The biodegradable resin particles according to claim 1, wherein the biodegradable resin particles have a coefficient of variation of particle diameters of less than or equal to 45%.

3. The biodegradable resin particles according to claim 1, wherein the biodegradable resin particles have an ash content of 0.01 to 3%, and the ash content is an ash content after the biodegradable resin particles are heated at 750° C. for 30 minutes.

4. The biodegradable resin particles according to claim 1, further comprising at least one of 3-alkoxy-3-methyl-1-butanol or 3-alkoxy-3-methyl-1-butyl acetate, wherein the alkoxy group has 1 to 5 carbon atoms.

5. The biodegradable resin particles according to claim 1, wherein the biodegradable resin particles have a volume average particle diameter of 8 to 20 μm.

6. An external preparation, comprising the biodegradable resin particles according to claim 1.

7. The external preparation according to claim 6, further comprising a non-volatile oil having a viscosity of less than or equal to 550 mPa·s at 20° C.

8. The external preparation according to claim 6, wherein the external preparation is a skin care cosmetic, a cleansing cosmetic, or a sunscreen cosmetic.

* * * * *